(12) United States Patent
Sriram et al.

(10) Patent No.: US 11,629,304 B2
(45) Date of Patent: Apr. 18, 2023

(54) SYNTHETIC LUBRICITY ADDITIVES FOR HYDROCARBON FUELS

(71) Applicant: ECOLAB USA INC., St. Paul, MN (US)

(72) Inventors: Suresh R. Sriram, Aurora, IL (US); Nestor U. Soriano, Jr., Missouri City, TX (US); Karina Eureste, Iowa Colony, TX (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 17/525,105

(22) Filed: Nov. 12, 2021

(65) Prior Publication Data

US 2022/0154089 A1     May 19, 2022

Related U.S. Application Data

(60) Provisional application No. 63/113,444, filed on Nov. 13, 2020.

(51) Int. Cl.
| | |
|---|---|
| *C10L 1/232* | (2006.01) |
| *C07D 207/404* | (2006.01) |
| *C10L 10/04* | (2006.01) |
| *C10L 10/08* | (2006.01) |

(52) U.S. Cl.
CPC .......... *C10L 1/232* (2013.01); *C07D 207/404* (2013.01); *C10L 10/04* (2013.01); *C10L 10/08* (2013.01); *C10L 2200/0446* (2013.01); *C10L 2200/0469* (2013.01)

(58) Field of Classification Search
CPC ..... C07D 207/404; C10L 10/04; C10L 10/08; C10L 1/232; C10L 1/2383; C10L 2200/0446; C10L 2200/0469
See application file for complete search history.

(56) References Cited

U.S. PATENT DOCUMENTS

| | | |
|---|---|---|
| 3,202,678 A | 8/1965 | Stuart et al. |
| 4,171,959 A | 10/1979 | Vartanian |
| 4,897,086 A | 1/1990 | Blain et al. |
| 5,551,957 A | 9/1996 | Cunningham et al. |
| 7,361,629 B2 | 4/2008 | Loper et al. |
| 9,011,556 B2 | 4/2015 | Scwab |
| 2003/0172584 A1 | 9/2003 | Henly et al. |
| 2008/0086935 A1 | 4/2008 | Cunningham et al. |
| 2017/0096611 A1 | 4/2017 | Stevenson et al. |
| 2017/0107438 A1 | 4/2017 | Greenfield et al. |
| 2017/0114297 A1* | 4/2017 | Sampler .................. C10L 1/221 |

FOREIGN PATENT DOCUMENTS

| | | |
|---|---|---|
| EP | 1303577 B1 | 1/2002 |
| EP | 1970430 A2 | 9/2008 |
| RU | 2540671 C2 | 1/2015 |
| WO | 95/10582 A1 | 4/1995 |

OTHER PUBLICATIONS

Farhad M Hossain, Thesis, "Experimental Investigation of Thermochemically-Derived Fuels in a Diesel Engine" Chemistry, Physics and Mechanical Engineering School Science and Engineering Faculty Queensland University of Technology, 2018, pp. 1-184.
PCT/US2021/059087, International Search Report and the Written Opinion of the International Searching Authority, dated Feb. 9, 2022, 11 pgs.

* cited by examiner

*Primary Examiner* — Ellen M McAvoy
*Assistant Examiner* — Chantel L Graham
(74) *Attorney, Agent, or Firm* — Kagan Binder, PLLC

(57) ABSTRACT

Lubricity additives for hydrocarbon fuels are provided according to formula I:

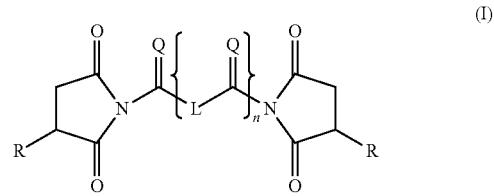

(I)

wherein n is 1 or 0; each Q is independently selected from oxygen and sulfur; each R is independently selected from C8-C60 alkenyl groups which are substituted or unsubstituted; and L is a linking group comprising 0-20 carbons which may be substituted or unsubstituted and may optionally comprise catenary heteroatoms. Fuel mixtures comprising a hydrocarbon fuel; and a lubricity additive according to the present disclosure are also provided. Methods of making lubricity additives comprise reacting an alkenyl succinic anhydrides (ASA's) with certain bisamides or bisthioamides.

18 Claims, No Drawings

SYNTHETIC LUBRICITY ADDITIVES FOR HYDROCARBON FUELS

Priority Claim

This U.S. Nonprovisional Application claims priority to U.S. Provisional Patent Application No. 63/113,444, filed Nov. 13, 2020, the content of which is incorporated herein by reference in its entirety.

FIELD OF THE DISCLOSURE

This disclosure relates to lubricity additives for hydrocarbon fuels including adducts of alkenyl succinic anhydrides (ASA's) and certain bisamides or bisthioamides.

BACKGROUND OF THE DISCLOSURE

Refiners utilize intensive fuel processing in order to meet the stringent government mandates limiting permissible levels of sulfur in finished fuels. At present in the United States, the maximum specification for ultra-low sulfur diesel (ULSD) is 15 ppm. USLD is the on-road diesel fuel in the US. Unfortunately, this intensive processing also eliminates trace oxygen and nitrogen compounds that contribute to the fuel's inherent lubricity. Hence ULSD is known to be less lubricating if not treated with lubricity improving additives. Lubrication is vital in preventing wear in fuel delivery systems, particularly in pumps, high pressure pumps, and injectors.

The majority of commercial lubricity additives are based on fatty acids of natural origin such as vegetable oils or plant oils, such as tall oil fatty acids (TOFA). As such, these lubricity additives are subjected to supply and cost constraints due to the inherent price volatility of these raw materials. Moreover, variabilities in qualities and properties of vegetable and plant-based oils in various regions create product quality inconsistencies. Hence, the development of 100% synthetic-based lubricity additives holds the potential to ease supply chain challenges, avoid significant raw material cost fluctuations, and ensure consistent product quality.

In addition to lubricity additives, hydrocarbon fuels such as diesel fuel may be formulated with additives to modify other characteristics of the fuel and its performance in an engine. Such additives may include dispersants, antioxidants, viscosity index modifiers, corrosion inhibitors, and the like.

U.S. Pat. No. 7,361,629 concerns a composition for use as an additive for fuels and lubricants that includes an amination product of a hydrocarbyl substituted succinic acylating agent and polyamines. U.S. Pat. No. 7,361,629 teaches the use of this additive as a dispersant to maintain impurities and deposits in a suspended state so that they can be removed from the system by filtration or other means rather than being deposited on internal engine components.

U.S. Pat. No. 5,551,957 concerns a fuel additive concentrate for use as a detergent/dispersant. The fuel additive concentrate includes a fuel-soluble product formed by reaction between (a) at least one polyamine and (b) at least one acyclic hydrocarbyl-substituted succinic acylating agent.

SUMMARY OF THE DISCLOSURE

Briefly, the present disclosure provides lubricity additives according to formula I:

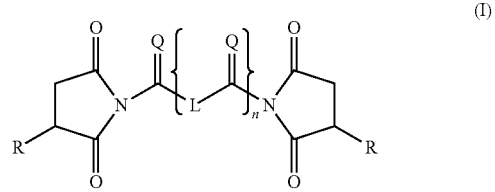

wherein n is 1 or 0; each Q is independently selected from oxygen and sulfur; each R is independently selected from C8-C60 alkenyl groups which are substituted or unsubstituted; and L is a linking group comprising 0-20 carbons which may be substituted or unsubstituted and may optionally comprise catenary heteroatoms (i.e., atoms in a carbon chain other than carbon, such as would render the group an ether, a secondary amine, etc.). In some embodiments each Q is oxygen, in some each Q is sulfur, and in some at least one Q is oxygen and at least one Q is sulfur. Additional embodiments of the lubricity additives of the present disclosure are described below.

In another aspect, the present disclosure provides fuel mixtures comprising a hydrocarbon fuel; and a lubricity additive according to the present disclosure. In various embodiments the hydrocarbon fuel may be a middle distillate fuel, derived from petroleum or biobased feedstock. Additional embodiments of the fuel mixtures of the present disclosure are described below.

In another aspect, the present disclosure provides methods of making lubricity additives comprising reacting an alkenyl succinic anhydride according to formula II:

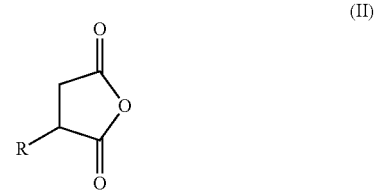

with a species according to formula III:

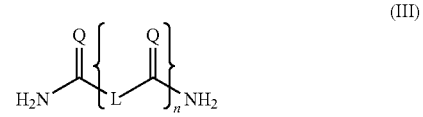

wherein R is a C8-C60 alkenyl group which is substituted or unsubstituted; n is 1 or 0; each Q is independently selected from oxygen and sulfur; and L is a linking group comprising 0-20 carbons which may be substituted or unsubstituted and may optionally comprise catenary heteroatoms. In some embodiments each Q is oxygen, in some each Q is sulfur, and in some at least one Q is oxygen and at least one Q is sulfur. Additional embodiments of the methods of the present disclosure are described below.

The preceding summary of the present disclosure is not intended to describe each embodiment of the present invention. The details of one or more embodiments of the invention are also set forth in the description below. Other features, objects, and advantages of the invention will be apparent from the description and from the claims.

In this application:

"common solvents" refers to low molecular weight organic liquids commonly used as solvents by practitioners in the art, which may include aliphatic and alicyclic hydrocarbons (e.g., hexane, heptane, and cyclohexane), aromatic solvents (e.g., benzene, toluene, xylene, and mixtures of heavy aromatic naphtha), ethers (e.g., diethyl ether, glyme, diglyme, diisopropyl ether, and tetrahydrofuran), esters (e.g., ethyl acetate and butyl acetate), alcohols (e.g., ethanol and isopropyl alcohol), ketones (e.g., acetone, methyl ethyl ketone, and methyl isobutyl ketone), sulfoxides (e.g., dimethyl sulfoxide), amides (e.g., N,N-dimethylformamide, N,N-dimethylacetamide, and N-methyl-2-pyrrolidone), halogenated solvents (e.g., methylchloroform, 1,1,2-trichloro-1,2,2-trifluoroethane, trichloroethylene, and trifluorotoluene), and mixtures thereof; and "substituted" means, for a chemical species, group or moiety, substituted by conventional substituents which do not interfere with the desired product or process, e.g., substituents can be alkyl, alkoxy, aryl, phenyl, halo (F, Cl, Br, I), cyano, nitro, etc.

All scientific and technical terms used herein have meanings commonly used in the art unless otherwise specified. All chemical formulas used herein are intended to include all enantiomers or stereoisomers unless otherwise specified.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

DETAILED DESCRIPTION

The present disclosure provides synthetic lubricity additives for hydrocarbon fuels such as diesel fuel. Lubricity additives may be species according to formula I:

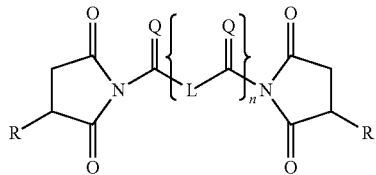

(I)

wherein n is 1 or 0; wherein each Q is independently selected from oxygen and sulfur; wherein each R is independently selected from C8-C60 alkenyl groups which are substituted or unsubstituted; and wherein L is a linking group comprising 1-20 carbons which may be substituted or unsubstituted and may optionally comprise catenary heteroatoms. In some embodiments each Q is oxygen, whereas in others each Q is sulfur, whereas in others at least one Q is oxygen and at least one Q is sulfur. In some embodiments n is 0. Where n is 1, L may comprise 0-10 carbons, 0-8 carbons, 0-6 carbons, or 0-4 carbons, 1-10 carbons, 1-8 carbons, 1-6 carbons, or 1-4 carbons and may or may not include catenary oxygen atoms (ether oxygens), and may or may not include catenary —NH— groups (amines). In various embodiments, L may be a straight-chain, branched, cyclic, saturated, unsaturated, or aromatic divalent group. In various embodiments, each R may be independently selected from straight-chain, branched, or cyclic groups. Each R may attach to one of the two succinyl groups of Formula I at a terminal carbon of the R group, or may attach to the succinyl group at a non-terminal carbon of the R group such that the R group branches at that carbon. In various embodiments, each R group may be independently selected from C8-C60 alkenyl groups, C10-C60 alkenyl groups, C12-C60 alkenyl groups, C14-C60 alkenyl groups, C16-C60 alkenyl groups, C18-C60 alkenyl groups, C20-C60 alkenyl groups, C21-C60 alkenyl groups, C8-C50 alkenyl groups, C10-C50 alkenyl groups, C12-C50 alkenyl groups, C14-C50 alkenyl groups, C16-C50 alkenyl groups, C18-C50 alkenyl groups, C20-C50 alkenyl groups, C21-C50 alkenyl groups, C8-C40 alkenyl groups, C10-C40 alkenyl groups, C12-C40 alkenyl groups, C14-C40 alkenyl groups, C16-C40 alkenyl groups, C18-C40 alkenyl groups, C20-C40 alkenyl groups, C21-C40 alkenyl groups, C8-C32 alkenyl groups, C10-C32 alkenyl groups, C12-C32 alkenyl groups, C14-C32 alkenyl groups, C16-C32 alkenyl groups, C18-C32 alkenyl groups, C20-C32 alkenyl groups, C21-C32 alkenyl groups, C8-C28 alkenyl groups, C10-C28 alkenyl groups, C12-C28 alkenyl groups, C14-C28 alkenyl groups, C16-C28 alkenyl groups, C18-C28 alkenyl groups, C20-C28 alkenyl groups, C21-C28 alkenyl groups, C8-C24 alkenyl groups, C10-C24 alkenyl groups, C12-C24 alkenyl groups, C14-C24 alkenyl groups, C16-C24 alkenyl groups, C18-C24 alkenyl groups, C20-C24 alkenyl groups, or C21-C24 alkenyl groups. Among lubricity additives according to the present disclosure having R groups in the range of C12-C24, we have found the longer-chain R groups to provide more effective lubricity additives that can outperform current commercial lubricity additives.

The present lubricity additives may be made by any suitable method. In one method, an alkenyl succinic anhydride (ASA) according to formula II:

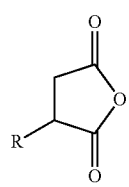

(II)

is reacted with a species according to formula III:

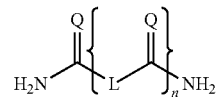

(III)

wherein R, n, Q, and L are as described above. In embodiments where Q is O and n is 0, the species according to formula III is urea. In embodiments where Q is S and n is 0, the species according to formula III is thiourea. In embodiments where Q is O and n is 1, the species according to formula III is a bisamide terminating at each end with a —C(O)NH$_2$ (amide) group. In embodiments where Q is S and n is 1, the species according to formula III is a bisthioamide terminating at each end with a —C(S)NH$_2$ (thioamide) group. In embodiments where Q is S, n is 1, and L contains 0 carbons, the species according to formula III is ethane bisthioamide, H$_2$NC(S)C(S)NH$_2$.

The alkenyl succinic anhydride (ASA) according to formula II may be made according to any suitable method. In one embodiment, a selected olefin is reacted with maleic anhydride under inert atmosphere at elevated temperature, as described below in the Examples. The selected olefin may be present in a slight molar excess to minimize the formation of polymaleic anhydride. The olefin may be an alpha olefin or an internal olefin having a carbon-carbon double bond available for reaction. The selected olefin may be a single species of olefin or a mixture of species.

The ASA may be reacted with the species according to formula III by any suitable method. In one embodiment, the two reactants are reacted under inert atmosphere at elevated temperature, as described below in the Examples.

Typically ASA and the species according to formula III are present in the reaction mixture in 2:1 molar ratio. In one embodiment, the reaction temperature is increased stepwise to provide amidation of ASA at lower temperatures, followed by ring closure to provide the corresponding imide groups at higher temperatures. Stepwise amidation and imidation was found to eliminate the formation of precipitates resulting from side-reactions.

The present method employing a bisamide (such as urea (IUPAC designation carbonyl diamide) results in a carbonyl group that provides increased binding to metal surfaces, a trait that is desirable in a lubricity additive.

The present fuel additives may be provided neat or in solution. Certain fuel additives may be gels or solids at room temperature in the absence of solvent, leading to difficulty in handling and in blending with fuel. For example, neat ASA-urea adducts are gels or solids at room temperature, depending on the length and the structure (e.g., branched or straight) of the alkenyl R groups. Formulations of these lubricity additives with as little as 10% solvent remain liquid and stable (i.e., no gelation, precipitation, phase separation, or dramatic increase in viscosity) during prolonged storage at 10° C. Any suitable common solvent may be used. In some embodiments, the solvent is an aromatic solvent such as heavy aromatic naphtha. Greater dilution may result in reduced viscosity and therefore improved pumpability at lower temperatures. Formulations of these lubricity additives with 20% solvent or 30% solvent demonstrate low viscosity at sub-zero (centigrade) temperatures and excellent performance as lubricity additives.

The present disclosure additionally provides fuel mixtures comprising a hydrocarbon fuel and a lubricity additive according to the present disclosure. Any suitable fuel may be used. In various embodiments, the hydrocarbon fuel may be a middle distillate fuel, a bio-sourced fuel, or a diesel fuel. The fuel mixture may additionally comprise other additives such as one or more of dispersants, antioxidants, viscosity index modifiers, corrosion inhibitors, and the like.

Additional embodiments are recited in the Selected Embodiments and Examples below.

Selected Embodiments

The following embodiments, designated by letter and number, are intended to further illustrate the present disclosure but should not be construed to unduly limit this disclosure.

A1. A lubricity additive according to formula I:

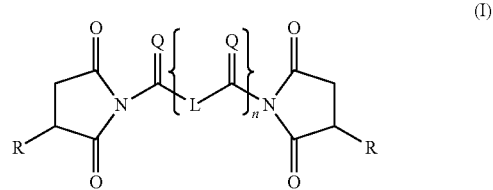

wherein n is 1 or 0;
wherein each Q is independently selected from oxygen and sulfur;
wherein each R is independently selected from C8-C60 alkenyl groups which are substituted or unsubstituted; and
wherein L is a linking group comprising 0-20 carbons which may be substituted or unsubstituted and may optionally comprise catenary heteroatoms.

A2. A lubricity additive according to embodiment A1 wherein each Q is oxygen.

A3. A lubricity additive according to embodiment A1 wherein each Q is sulfur.

A4. A lubricity additive according to any of embodiments A1-A3 wherein n is 0.

A5. A lubricity additive according to any of embodiments A1-A4 wherein each R is independently selected from straight-chain or branched groups.

A6. A lubricity additive according to any of embodiments A1-A4 wherein each R is independently selected from straight-chain groups.

A7. A lubricity additive according to any of embodiments A1-A4 wherein each R is independently selected from branched groups.

A8. A lubricity additive according to any of embodiments A1-A7 wherein each R is independently selected from C8-C32 alkenyl groups.

A9. A lubricity additive according to any of embodiments A1-A7 wherein each R is independently selected from C12-C32 alkenyl groups.

A10. A lubricity additive according to any of embodiments A1-A7 wherein each R is independently selected from C18-C32 alkenyl groups.

A11. A lubricity additive according to any of embodiments A1-A7 wherein each R is independently selected from C12-C24 alkenyl groups.

A12. A lubricity additive according to any of embodiments A1-A7 wherein each R is independently selected from C20-C24 alkenyl groups.

F1. A fuel mixture comprising:
  a) a hydrocarbon fuel; and
  b) a lubricity additive according to any of embodiments A1-A12.

F2. A fuel mixture according to embodiment F1 wherein the hydrocarbon fuel is a middle distillate fuel.

F3. A fuel mixture according to embodiment F1 wherein the hydrocarbon fuel is a bio-based fuel.

F4. A fuel mixture according to embodiment F1 wherein the hydrocarbon fuel is a diesel fuel.

M1. A method of making a lubricity additive comprising reacting an alkenyl succinic anhydride according to formula II:

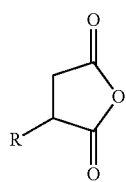

with a species according to formula III:

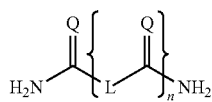

wherein R is a C8-C60 alkenyl group which is substituted or unsubstituted;
wherein n is 1 or 0;
wherein each Q is independently selected from oxygen and sulfur; and
wherein L is a linking group comprising 0-20 carbons which may be substituted or unsubstituted and may optionally comprise catenary heteroatoms.

M2. A method according to embodiment M1 wherein each Q is oxygen.

M3. A method according to embodiment M1 wherein each Q is sulfur.

M4. A method according to any of embodiments M1-M3 wherein n is 0.

M5. A method according to any of embodiments M1-M4 wherein the lubricity additive is a lubricity additive according to any of embodiments A1-A12.

Objects and advantages of this disclosure are further illustrated by the following examples, but the particular materials and amounts thereof recited in these examples, as well as other conditions and details, should not be construed to unduly limit this disclosure.

EXAMPLES

Unless otherwise noted, all reagents were obtained or are available from Aldrich Chemical Co., Milwaukee, Wis., or may be synthesized by known methods.

All parts, percentages, ratios, etc. in the examples and the rest of the specification are by weight, unless noted otherwise. The following abbreviations may be used: m=meters; cm=centimeters; mm=millimeters; um=micrometers; ft=feet; in =inch; RPM=revolutions per minute; kg=kilograms; oz=ounces; lb=pounds; Pa=Pascals; sec=seconds; min=minutes; hr=hours; and RH=relative humidity. The terms "weight %", "% by weight", and "wt %" are used interchangeably.

| Materials | |
|---|---|
| Designation | Description |
| maleic anhydride | maleic anhydride obtained from Huntsman Corporation, USA, under the designation Low Acid Maleic Anhydride. |
| urea | Urea obtained from Univar Inc., USA, under the designation designation Urea Prill. |
| heavy aromatic naphtha | heavy aromatic naphtha obtained from ExxonMobil Chemical, USA, under the brand name SOLVESSO™ 150. |
| C12 olefin | Dodecene obtained from Shell Inc., USA, under the brand name NEODENE™ 12. |
| C18 olefin | Octadecene obtained from Shell Inc., USA, under the brand name NEODENE™ 18. |
| C12-C14 alpha-olefin | Isomerized Alpha Olefin C12-C14 obtained from Chevron Phillips Chemical Company, USA, under the designation Isomerized Alpha Olefin C12-C14. |
| C16-C18 internal olefin | Isomerized Alpha Olefin C16-C18 Mixture obtained from Chevron Phillips Chemical Company, USA, under the designation Isomerized Alpha Olefin C16-C18. |
| C20-C24 olefin | Isomerized Alpha Olefin C20-C24 Mixture obtained from Chevron Phillips Chemical Company, USA, under the designation Isomerized Alpha Olefin C20-C24. |
| C-18 ASA | C-18 alkenyl succinic anhydride obtained from Bercen Inc, USA, under the brand name BERSIZE™ 7938 |
| C-20-24 ASA | C-20-24 alkenyl succinic anhydride mixture obtained from Bercen Inc, USA, under the brand name BERSIZE™ 2024 |
| C-12 ASA | C-12 alkenyl succinic anhydride obtained from Milliken & Company, USA, under the designation DDSA. |
| Domestic Summer ULSD | Ultra-Low Sulfur Diesel fuel in a domestic use summer formulation |
| Domestic Winter ULSD | Ultra-Low Sulfur Diesel fuel in a domestic use winter formulation |
| Export Summer ULSD | Ultra-Low Sulfur Diesel fuel in an export summer formulation |

-continued

| Materials | |
|---|---|
| Designation | Description |
| Export Winter ULSD | Ultra-Low Sulfur Diesel fuel in an export winter formulation |
| Benchmark Lubricity Additive | Non-synthetic obtained from Nalco Company, Naperville, Illinois, under the designation EC5720A. |
| Ethanolamine | Ethanolamine obtained from Dow Chemical Corp, Freeport, TX. |
| Biuret | $H_2N-C(O)-NH-C(O)-NH_2$ obtained from VWR Inc. Radnor, PA. |
| Oleylpropanediamine | N-Oleyl-1,3-diaminopropane obtained from Noury on Surface Chemistry LLC, Chicago, IL, under the designation DUOMEEN™ OL |
| Glycerol | glycerine obtained from Vantage Oleochemicals, Chicago, IL under the designation VYCERIN™ GL93. |

Synthesis of Alkenyl Succinic Anhydrides (ASA's)

Maleic anhydride was pulverized and then melted in a flask at 80° C. under nitrogen sweep to purge the oxygen in the system. The selected olefin was charged into the flask in a slight molar excess to minimize the formation of polymaleic anhydride, which is a side reaction.

Polymaleic anhydride may appear as dark brown precipitate which is discarded. The reaction mixture was heated to 200° C.-205° C. for at least 10 hours under nitrogen to generate the corresponding alkenyl succinic anhydride (ASA) as an amber to dark amber viscous liquid.

Synthesis of ASA-Urea Adducts

Following the ASA synthesis the flask was cooled to 100° C. Urea was added in a 2:1 ASA/urea molar ratio. The temperature was increased stepwise with a 2 hour duration at each of 100° C., 120° C., and 140° C.-150° C. The stepwise increase in temperature during imidation provided amidation of ASA with urea at lower temperatures, followed by ring closure to afford the corresponding ASA-urea adduct at higher temperatures (≥140° C.). Stepwise amidation and imidation was found to eliminate the formation of black precipitate. After a total of 6 hours reaction time as described above, heavy aromatic naphtha was charge into the flask followed by filtration to afford a formulation at the desired concentration.

High Frequency Reciprocating Rig (HFRR) Test Method

HFRR testing was performed in accordance with ASTM D6079 Standard Test Method for Evaluating Lubricity of Diesel Fuels by the High-Frequency Reciprocating Rig (HFRR).

HFRR Results

Examples 1-4 and Comparative Examples C1-C2

Table I reports HFRR results demonstrating lubricity improvement (smaller wear scar) with the use of ASA-Urea Adducts made with the C12 olefin (Ex. 1 and 3) or the C18 olefin (Ex. 2 and 4). For comparative examples C1 and C2, the unreacted C12 olefin alone was used as the additive. The "Comparative Wear Scar" column reports results obtained under the same conditions using the Benchmark Lubricity Additive. All additive formulations were 50% by weight additive in heavy aromatic naphtha, which is comparable to the Benchmark Lubricity Additive. The indicated additive was used to treat ULSD fuels at the indicated concentration and tested in accordance with the HFRR Test Method. The treat rates described in Table 1 were based on the total amount of the formulated additives (including solvent).

Both ULSD's responded very well to the ASA-Urea adducts. On the other hand, the ULSD samples did not show the same respond to the unmodified alkenyl succinic anhydride suggesting that the incorporation of the imide functionality in the molecule is essential to achieve performance as a lubricity improver for ULSD.

TABLE 1

| Example | Active Material | ULSD | Treat Rate (ppm) | Example Wear Scar (μm) | Comparative Wear Scar (μm) |
|---|---|---|---|---|---|
| 1 | C12 ASA-Urea Adduct | Domestic Summer | 0 | 580 | 580 |
| | | | 200 | 511 | 510 |
| | | | 300 | 484 | 494 |
| 2 | C18 ASA-Urea Adduct | Domestic Summer | 0 | 580 | 580 |
| | | | 200 | 462 | 510 |
| | | | 300 | 415 | 494 |
| C1 | C12 ASA | Domestic Summer | 0 | 580 | 580 |
| | | | 200 | 547 | 510 |
| | | | 300 | 517 | 494 |
| 3 | C12 ASA-Urea Adduct | Export Winter | 0 | 578 | 578 |
| | | | 200 | 503 | 500 |
| | | | 350 | 428 | 369 |
| 4 | C18 ASA-Urea Adduct | Export Winter | 0 | 578 | 578 |
| | | | 200 | 447 | 500 |
| | | | 350 | 397 | 369 |
| C2 | C12 ASA | Export Winter | 0 | 578 | 578 |
| | | | 200 | 506 | 500 |
| | | | 350 | 503 | 369 |

Examples 5-8

Table 2 reports HFRR results demonstrating lubricity improvement (smaller wear scar) with the use of ASA-Urea Adducts made with the C12-C14 alpha-olefin (Ex. 5 and 6) or the C16-C18 internal olefin (Ex. 7 and 8), maleic anhydride, and urea as described above. As above, the "Comparative Wear Scar" column reports results obtained under the same conditions using the Benchmark Lubricity Additive. All additive formulations were 50% by weight additive in heavy aromatic naphtha, except examples 5 and 6 where the additive was added neat. In all cases, the Benchmark Lubricity Additive contains comparable % active as the formulated additives. The indicated additive was used to treat ULSD fuels at the indicated concentration and tested in accordance with the HFRR Test Method. The treat rates described in Table 2 were based on the total amount of the formulated additives (including solvent).

TABLE 2

| Example | Active Material | ULSD | Treat Rate (ppm) | Example Wear Scar (μm) | Comparative Wear Scar (μm) |
|---|---|---|---|---|---|
| 5 | C12-C14 ASA-Urea | Domestic Summer | 0 | 580 | 580 |
|  |  |  | 100 | 491 | 507 |
|  |  |  | 150 | 435 | 441 |
| 6 | C12-C14-ASA Urea | Domestic Winter | 0 | 571 | 571 |
|  |  |  | 100 | 511 | 501 |
|  |  |  | 150 | 448 | 450 |
| 7 | C16-C18 ASA-Urea | Domestic Summer | 0 | 580 | 580 |
|  |  |  | 200 | 526 | 510 |
|  |  |  | 300 | 459 | 494 |
| 8 | C16-C18 ASA-Urea | Export Winter | 0 | 578 | 578 |
|  |  |  | 200 | 498 | 500 |
|  |  |  | 350 | 416 | 369 |

Examples 9-14

To investigate the impact of ASA chain length on lubricity additive performance, ASA-Urea adducts derived from varying chain length olefins were tested as described above with regard to Examples 1-8 and the results are reported in Table 3. In general, it was found that better performance correlated with longer chain length.

TABLE 3

| Example | Active Material | ULSD | Treat Rate (ppm) | Example Wear Scar (μm) | Comparative Wear Scar (μm) |
|---|---|---|---|---|---|
| 9 | C12 ASA-Urea | Domestic Summer | 0 | 580 | 580 |
|  |  |  | 200 | 532 | 510 |
|  |  |  | 300 | 452 | 494 |
| 10 | C18 ASA-Urea | Domestic Summer | 0 | 580 | 580 |
|  |  |  | 200 | 497 | 510 |
|  |  |  | 300 | 432 | 494 |
| 11 | C20-C24 ASA-Urea | Domestic Summer | 0 | 580 | 580 |
|  |  |  | 200 | 468 | 510 |
|  |  |  | 300 | 424 | 494 |
| 12 | C12 ASA-Urea | Export Winter | 0 | 578 | 578 |
|  |  |  | 200 | 476 | 500 |
|  |  |  | 350 | 399 | 369 |
| 13 | C18 ASA-Urea | Export Winter | 0 | 578 | 578 |
|  |  |  | 200 | 482 | 500 |
|  |  |  | 350 | 381 | 369 |
| 14 | C20-C24 ASA-Urea | Export Winter | 0 | 578 | 578 |
|  |  |  | 200 | 449 | 500 |
|  |  |  | 350 | 381 | 369 |

Example 15: ASA-Urea Bisimide with Ethanolamine

A reaction was carried out according to the following procedure. C-18 ASA (58.36 g, 0.17 mol) and urea (5 g, 0.08 mol) were weighed into a 250 mL round-bottom reactor provided with an inert gas atmosphere to prevent oxidation. To the reaction mixture was added 25.87 g of heavy aromatic naphtha (HAN) and ethanolamine (1.27 g, 0.0208 mol) and stirred. The mixture was heated to 90° C. while stirring using a heated oil bath. After 4 hours the reaction temperature was raised to 150° C. and held at 150° C. for 4 hours. After the total reaction time of 8 hours, the principally Bisimide product (Bisimide, 58 g, 96%) was obtained. The product was obtained as a clear amber yellow liquid at 70% concentration in heavy aromatic naphtha. This concentration is useful for ease of handling. The additive at the appropriate concentration can be added to the diesel fuel to obtain the desired lubricity performance. The lubricity performance of the product was measured in the high frequency reciprocating rig (HFRR) as described above and demonstrated wear scar values of 379 μm at 250 ppm concentration in diesel fuel.

Example 16: ASA-Biuret Bisimide with Ethanolamine

A reaction was carried out according to the following procedure. C-18 ASA (54.41 g, 0.16 mol) and Biuret (8 g, 0.08 mol) were weighed into a 250 mL round-bottom reactor provided with an inert gas atmosphere to prevent oxidation. To the reaction mixture was added 25.9 g of heavy aromatic naphtha (HAN) and ethanolamine (1.39 g, 00217 mol) and stirred. The mixture was heated to 90° C. while stirring using a heated oil bath. After 4 hours the reaction temperature is raised to 150° C. and held at 150° C. for 4 hours. After the total reaction time of 8 hours, the principally Bisimide product (Bisimide, 56 g, 94%) was obtained. The product is obtained as a clear dark amber liquid at 70% concentration in heavy aromatic naphtha. This concentration is useful for ease of handling. The additive at the appropriate concentration can be added to the diesel fuel to obtain the desired lubricity performance. The lubricity performance of the product was measured in the high frequency reciprocating rig (HFRR) as described above and demonstrated wear scar values in the range of 370 μm at a 250 ppm concentration in the diesel fuel.

Example 17: ASA-Urea Bisimide with Oleylpropandiamine

A reaction was carried out according to the following procedure. C-18 ASA (58.36 g, 0.17 mol) and urea (5 g, 0.08 mol) were weighed into a 250 mL round-bottom reactor provided with an inert gas atmosphere to prevent oxidation. To the reaction mixture was added 25.87 g of heavy aromatic naphtha (HAN) and oleylpropandiamine (1.27 g, 004 mol) and stirred. The mixture was heated to 90° C. while stirring using a heated oil bath. After 4 hours the reaction temperature is raised to 150° C. and held at 150° C. for 4 hours. After the total reaction time of 8 hours, the Bisimide product (Bisimide, 58 g, 96%) was obtained. The product is obtained as a clear amber yellow liquid at 70% concentration in heavy aromatic naphtha. This concentration is useful for ease of handling. The additive at the appropriate concentration can be added to the diesel fuel to obtain the desired lubricity performance. The lubricity performance of the product was measured in the high frequency reciprocating rig (HFRR) as described above and demonstrated wear scar values of 378 μm at a 250 ppm concentration in the diesel fuel.

Example 18

Alkenyl succinic glycerol bisester derivatives were synthesized from the reaction of several alkenyl succinic anhydrides and glycerol through the ring opening reaction of the anhydride with glycerol. Final target products were a mixture of isomers, were characterized by 1H NMR, Fourier transform-infrared spectroscopy (FT-IR), and were used as additives without further purification.

A reaction was carried out according to the following procedure. C-18 ASA (55 g, 0.1569 mol) and glycerol (7.22 g, 0.0785 mol) were weighed into a 250 mL round-bottom reactor with an inert gas atmosphere to prevent oxidation. The mixture was heated to 70-80° C. while stirring using a heated oil bath. Products (Bisester, 61 g, 98%) were obtained after 8 hours. The product can be diluted with heavy aromatic naphtha to generate a concentrated product solution for ease of handling. The additive at the appropriate concentration can be added to the diesel fuel to obtain the desired lubricity performance. The lubricity performance of the product was measured in the high frequency reciprocating rig (HFRR) as described above and demonstrated wear scar values in the range of 368-404 μm at a 200 ppm concentration in the diesel fuel.

Example 19—Ferrous Corrosion Inhibitor Performance

Most fuel system storage tanks, transfer lines, and underground pipelines are composed of 1018/1020 carbon steel. These system components are all susceptible to internal corrosion when exposed to fuel containing water. Corrosion in fuel storage and transportation system can be aggravated by acid carryover from fuel processing, microbial growth, seawater contamination, and water from salt drying operations.

Lubricity improvers for diesel fuel are known to exhibit ferrous corrosion inhibitor activity at dosages required to meet the lubricity specification. However, commercial ferrous corrosion inhibitors typically are used at lower rates, typically from 1 to 15 ppm in fuels. At these rates, typical lubricity improvers do not demonstrate good performance as corrosion inhibitors.

NACE TM 0172 Standard Test Method for Determining Corrosive Properties of Cargoes in Petroleum Product Pipelines is a test method used for fuel pipeline companies and refineries to determine the corrosive properties of liquid petroleum products and other hydrocarbon products that are not water-soluble for transporting through a steel pipeline. Typically, an A or B++ rating per NACE TM 0172 is considered acceptable.

The C-18 ASA/urea adduct described above was evaluated for ferrous corrosion inhibitor activity per NACE TM 0172 test in a corrosive summer diesel fuel and gasoline. The fuel samples were treated in the range of 1 to 10 ppm (based on 70% C-18 ASA/urea adduct in heavy aromatic naphtha). Tables 4 and 5 report the NACE TM 0172 performance of C-the 18 ASA/urea adduct as corrosion inhibitor.

TABLE 4

C-18 ASA/urea adduct (70% active) ferrous corrosion inhibitor performance per NACE TM 0172 in a summer diesel fuel.

| Treat Rate, ppm | NACE Rating per TM 0172 |
| --- | --- |
| 0 | B+ |
| 5 | A |
| 10 | A |
| 15 | A |

TABLE 5

C-18 ASA/urea adduct (70% active) ferrous corrosion inhibitor performance per NACE TM 0172 in gasoline.

| Treat Rate, ppm | NACE Rating per TM 0172 |
| --- | --- |
| 0 | C |
| 1 | A |

TABLE 5-continued

C-18 ASA/urea adduct (70% active) ferrous corrosion inhibitor performance per NACE TM 0172 in gasoline.

| Treat Rate, ppm | NACE Rating per TM 0172 |
| --- | --- |
| 5 | A |
| 10 | A |

Various modifications and alterations of this disclosure will become apparent to those skilled in the art without departing from the scope and principles of this disclosure, and it should be understood that this disclosure is not to be unduly limited to the illustrative embodiments set forth hereinabove.

We claim:

1. A lubricity additive according to formula I:

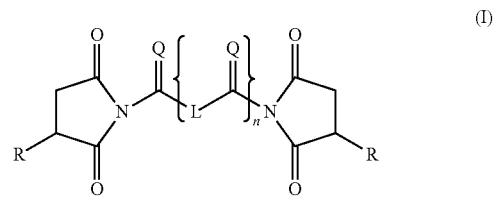

wherein n is 1 or 0;

wherein each Q is independently selected from oxygen and sulfur;

wherein each R is independently selected from C8-C60 alkenyl groups which are substituted or unsubstituted; and wherein L is a linking group comprising 0-20 carbons which may be substituted or unsubstituted and may optionally comprise catenary heteroatoms.

2. A lubricity additive according to claim 1 wherein each Q is oxygen.

3. A lubricity additive according to claim 1 wherein each Q is sulfur.

4. A lubricity additive according to claim 1 wherein n is 0.

5. A lubricity additive according to claim 1 wherein each R is independently selected from C12-C32 alkenyl groups.

6. A lubricity additive according to claim 1 wherein each R is independently selected from C12-C24 alkenyl groups.

7. A lubricity additive according to claim 1 wherein each R is independently selected from C20-C24 alkenyl groups.

8. A fuel mixture comprising:

a) a hydrocarbon fuel; and b) a lubricity additive according to claim 1.

9. A fuel mixture according to claim 8 wherein the hydrocarbon fuel is a middle distillate fuel.

10. A fuel mixture according to claim 8 wherein the hydrocarbon fuel is a diesel fuel derived from petroleum or biobased feedstock.

11. A method of making a lubricity additive comprising reacting an alkenyl succinic anhydride according to formula II:

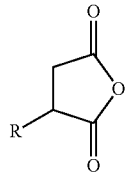
(II)

with a species according to formula III:

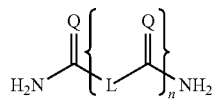
(III)

wherein R is a C8-C60 alkenyl group which is substituted or unsubstituted;
wherein n is 1 or 0;
wherein each Q is independently selected from oxygen and sulfur; and
wherein L is a linking group comprising 0-20 carbons which may be substituted or unsubstituted and may optionally comprise catenary heteroatoms.

12. A method according to claim 11 wherein each Q is oxygen.

13. A method according to claim 11 wherein each Q is sulfur.

14. A method according to claim 11 wherein n is 0.

15. A lubricity additive according to claim 2 wherein n is 0.

16. A fuel mixture comprising:
a) a hydrocarbon fuel; and
b) a lubricity additive according to claim 2.

17. A fuel mixture according to claim 16 wherein the hydrocarbon fuel is a middle distillate fuel.

18. A method according to claim 12 wherein n is 0.

* * * * *